US008897528B2

(12) United States Patent
Benson et al.

(10) Patent No.: US 8,897,528 B2
(45) Date of Patent: Nov. 25, 2014

(54) SYSTEM AND METHOD FOR ITERATIVE IMAGE RECONSTRUCTION

(75) Inventors: Thomas Matthew Benson, Smyrna, GA (US); Bruno Kristiaan Bernard De Man, Clifton Park, NY (US); Lin Fu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 651 days.

(21) Appl. No.: 13/174,461

(22) Filed: Jun. 30, 2011

(65) Prior Publication Data

US 2011/0262054 A1    Oct. 27, 2011

Related U.S. Application Data

(63) Continuation-in-part of application No. 11/474,613, filed on Jun. 26, 2006, now Pat. No. 8,571,287.

(51) Int. Cl.
G06K 9/00 (2006.01)
G01N 23/04 (2006.01)
G06T 11/00 (2006.01)
A61B 6/03 (2006.01)

(52) U.S. Cl.
CPC .............. *G01N 23/046* (2013.01); *A61B 6/03* (2013.01); *G06T 2211/424* (2013.01); *G06T 11/006* (2013.01)
USPC .......................................... 382/131; 600/407

(58) Field of Classification Search
USPC .......................................... 382/131; 600/407
See application file for complete search history.

(56) References Cited

U.S. PATENT DOCUMENTS

| 6,148,056 A | 11/2000 | Lin et al. |
|---|---|---|
| 6,507,633 B1 | 1/2003 | Elbakri et al. |
| 7,671,891 B2 * | 3/2010 | Fitzgibbon et al. ........... 348/188 |
| 8,388,547 B2 * | 3/2013 | Revishvili et al. ........... 600/508 |
| 2008/0170126 A1 * | 7/2008 | Tico et al. .................. 348/208.6 |
| 2011/0307438 A1 * | 12/2011 | Fernández Martínez ....... 706/52 |
| 2014/0010431 A1 * | 1/2014 | Stayman et al. .............. 382/131 |

FOREIGN PATENT DOCUMENTS

| DE | 10200901472 A1 | 9/2010 |
|---|---|---|
| WO | 02067201 A1 | 8/2002 |

OTHER PUBLICATIONS

Stayman et al., "Efficient Calculation of Resolution and Covariance for Penalized-Likelihood Reconstruction in Fully 3-D Spect", IEEE Transactions on Medical Imaging, vol. 23, No. 12, Dec. 2004, 1543-1556.*

(Continued)

*Primary Examiner* — Jason Repko
*Assistant Examiner* — Katrina Fujita
(74) *Attorney, Agent, or Firm* — Fletcher Yoder, P.C.

(57) ABSTRACT

Methods are provided for iteratively reconstructing an image signal to generate a reconstructed image signal. In one embodiment, sub-iterations of each iteration are performed on pixel or voxel subsets. The subsets may be composed of neighboring or spatially separated pixel or voxels and may extend in the z-direction. In one embodiment, an update step of the iterative reconstruction involves the direct inversion of an approximation of a Hessian matrix associated with the respective subsets. In further embodiments, non-negativity or other limitations or constraints on update values may be enforced.

20 Claims, 11 Drawing Sheets

(56) References Cited

OTHER PUBLICATIONS

Fessler et al., "Spatial Resolution Properties of Penalized-Likelihood Image Reconstruction: Space-Invariant Tomographs", IEEE Transactions on Image Processing, vol. 5, No. 9. Sep. 1996, 1346-1358.*

Elbakri, Idris A., et al.; "Statistical X-Ray Computed Tomography Image Reconstruction with Beam Hardening Correction", Medical Imaging 2001, Proc. SPIE, vol. 4322; pp. 1-11.

Bertero, M.; "Iterative Image Reconstruction: A point of view", Proc. of IMRT, Oct. 2007; pp. 1-25.

* cited by examiner

SYSTEM AND METHOD FOR ITERATIVE IMAGE RECONSTRUCTION

CROSS-REFERENCE TO RELATED APPLICATIONS

This application is a continuation-in-part of U.S. patent application Ser. No. 11/474,613, entitled "System and Method for Iterative Image Reconstruction", filed Jun. 26, 2006, which is herein incorporated by reference in its entirety for all purposes.

BACKGROUND

Non-invasive imaging broadly encompasses techniques for generating images of the internal structures or regions of a person that are otherwise inaccessible for visual inspection. One of the best known uses of non-invasive imaging is in the medical arts where these techniques are used to generate images of organs and/or bones inside a patient which would otherwise not be visible. Other well known uses are in the field of non-destructive testing, such as for security and package screening or for quality control of manufacturing processes. Example of such non-invasive imaging modalities include X-ray based techniques, such as computed tomography (CT), as well as nuclear based technique, such as positron emission tomography (PET) and single photon emission computed tomography (SPECT).

With regard to CT imaging techniques, CT scanners operate by projecting fan shaped or cone shaped X-rays from an X-ray source. The X-ray source emits X-rays at numerous angles relative to an object being imaged, such as a patient, which attenuates the X-rays as they pass through. The attenuated X-rays are detected by a set of detector elements, which produce signals representing the attenuation of the incident X-rays. The signals are processed and reconstructed to form images which may be evaluated themselves or which may be associated to form a volume rendering or other representation of the imaged region. In a medical context, pathologies or other structures of interest may then be located or identified from the reconstructed images or rendered volume.

CT reconstruction is usually performed using direct reconstruction techniques, e.g., back-projection or filtered back-projection, based on mathematical ideals that are not typically observed in practice. One side effect of the failure of the mathematical ideals to correspond to actual practice is that noise and resolution performance for a given X-ray dose is typically not optimized using direct reconstruction techniques.

Iterative reconstruction techniques overcome these problems by employing various mathematical models, such as noise and system models, to account for deviations from the mathematical ideals. Iterative reconstruction techniques repeatedly apply respective forward and backward projection models to generate an image that best fits the image measurements according to an appropriate objective function. In this manner, iterative reconstruction algorithms may provide improved image quality and/or allow for reduced X-ray dosage. In addition, iterative reconstruction algorithms may provide other benefits, such as reduction of metal artifacts in reconstructed images.

However, iterative reconstruction algorithms require significantly more computation than conventional, i.e., direct, reconstruction methods where a single back-projection operation may be employed. In particular, iterative reconstruction algorithms undergo multiple iterations to generate each image, i.e., to converge. Further, each iteration employs two or more computationally intensive projection and back-projection operations. As a result, iterative reconstruction algorithms may require an order of magnitude or more computational effort than a direct reconstruction technique to construct a single image. Consequently, iterative reconstruction approaches are typically much slower than comparable direct reconstruction approaches.

BRIEF DESCRIPTION

A method is provided for iteratively reconstructing image data. The method includes accessing an initial image and defining a plurality of image element subsets of the initial image. Updates to the initial image or a subsequent updated image are iteratively generated based on the respective image element subsets. At least one of the updates is generated by directly inverting a respective Hessian matrix or an approximation of a respective Hessian matrix associated with a corresponding image element subset. The iterative generation of updates is terminated upon satisfaction of a completion criterion.

One or more non-transitory machine readable media are provided. The machine-readable media encode one or more routines which, when executed by a processor, perform acts comprising: generating an initial image; iteratively updating a plurality of image element subsets of the initial image or a subsequent updated image, wherein one or more of the updates is generated by directly inverting a respective Hessian matrix or an approximation of a respective Hessian matrix associated with a corresponding image element subset; and terminating the iterative generation of updates upon satisfaction of a completion criterion.

An additional method for iteratively reconstructing image data is provided. The method includes the act of accessing an initial image and iteratively updating a plurality of image element subsets of the initial image or a subsequent updated image. The iteratively generated updates are limited such that the updates, when applied, do not result in values outside of a specified range. For example, in some instances the updates will be restricted so that they do not produce negative values. The iterative generation of updates is terminated upon satisfaction of a completion criterion.

DRAWINGS

These and other features, aspects, and advantages of the present invention will become better understood when the following detailed description is read with reference to the accompanying drawings in which like characters represent like parts throughout the drawings, wherein.

Figure 8:
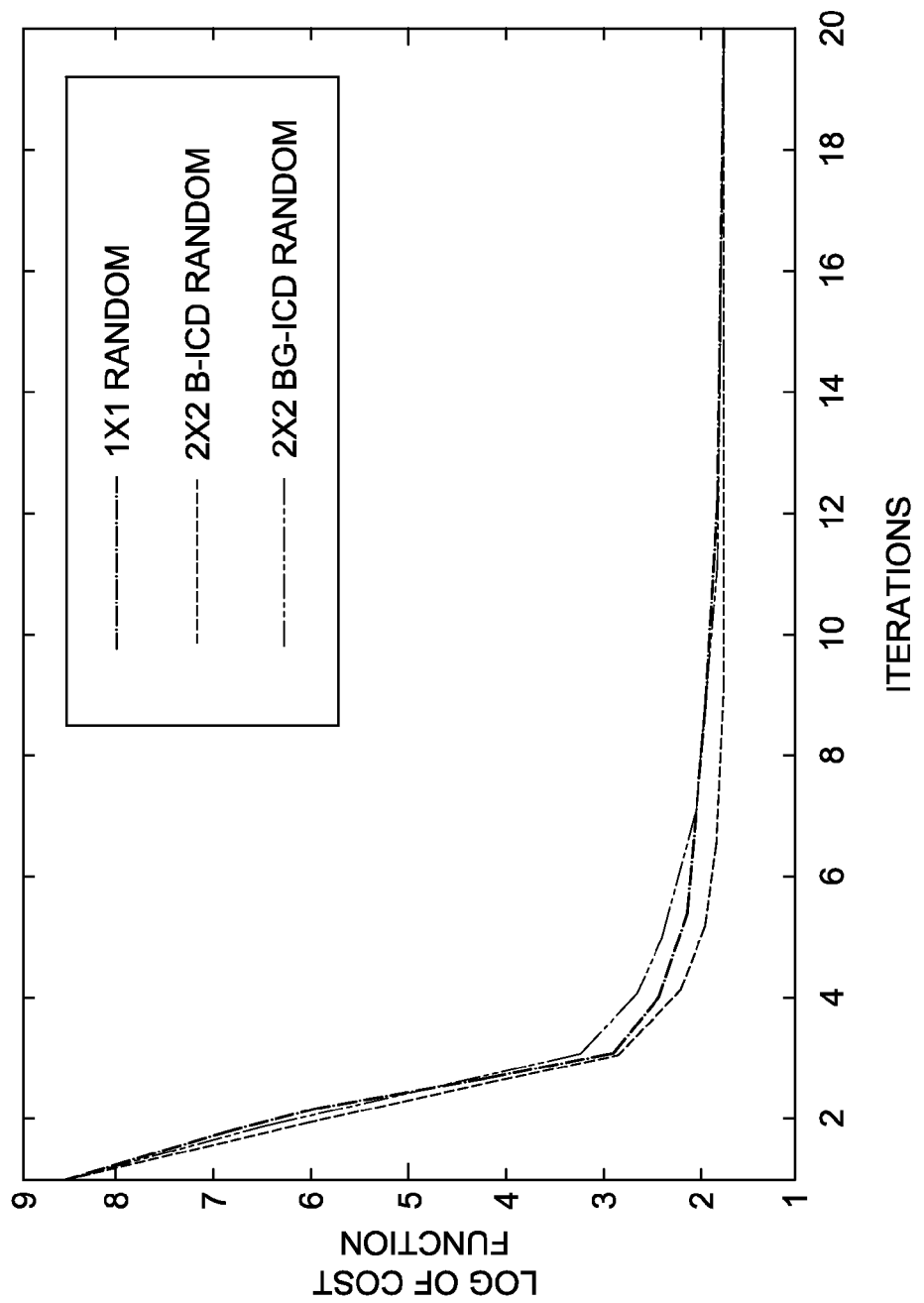
Figure 9:
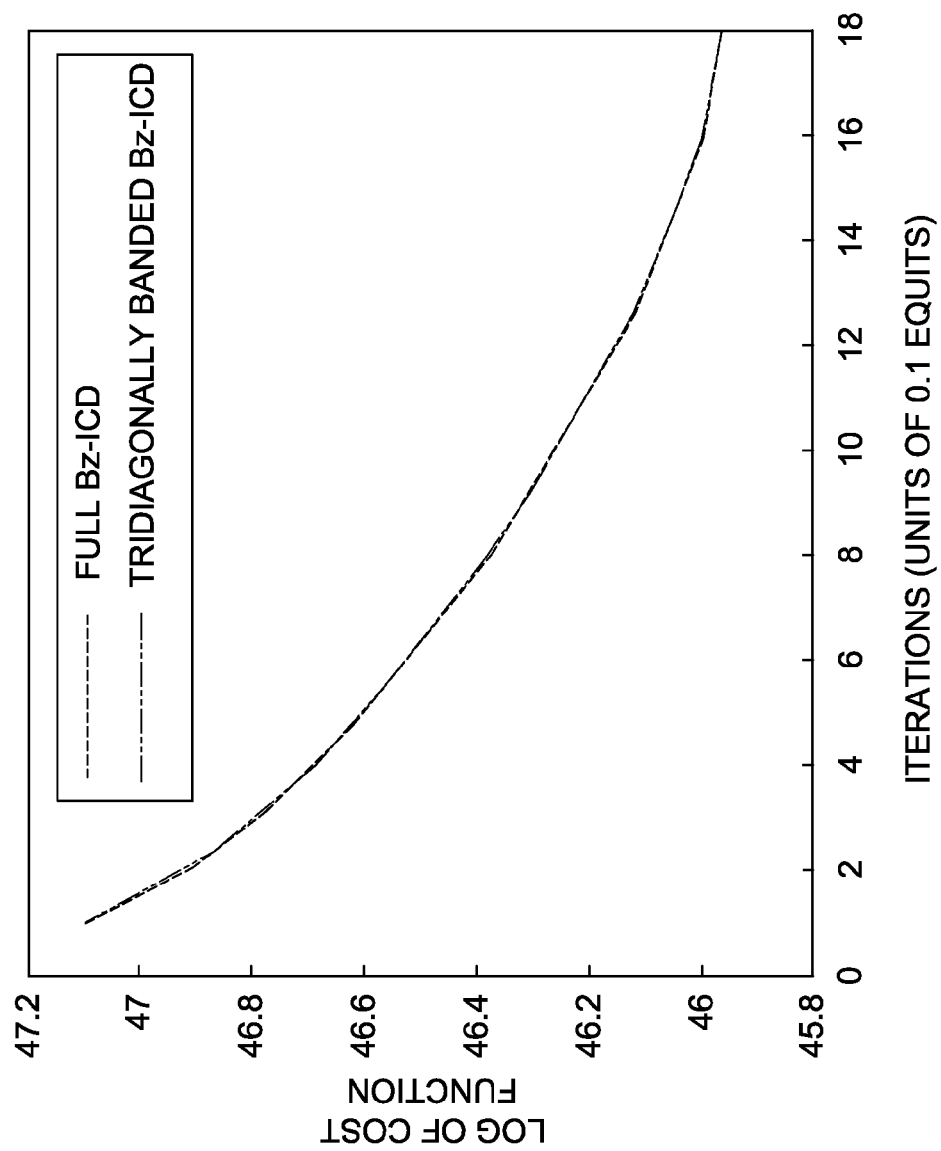
Figure 10:
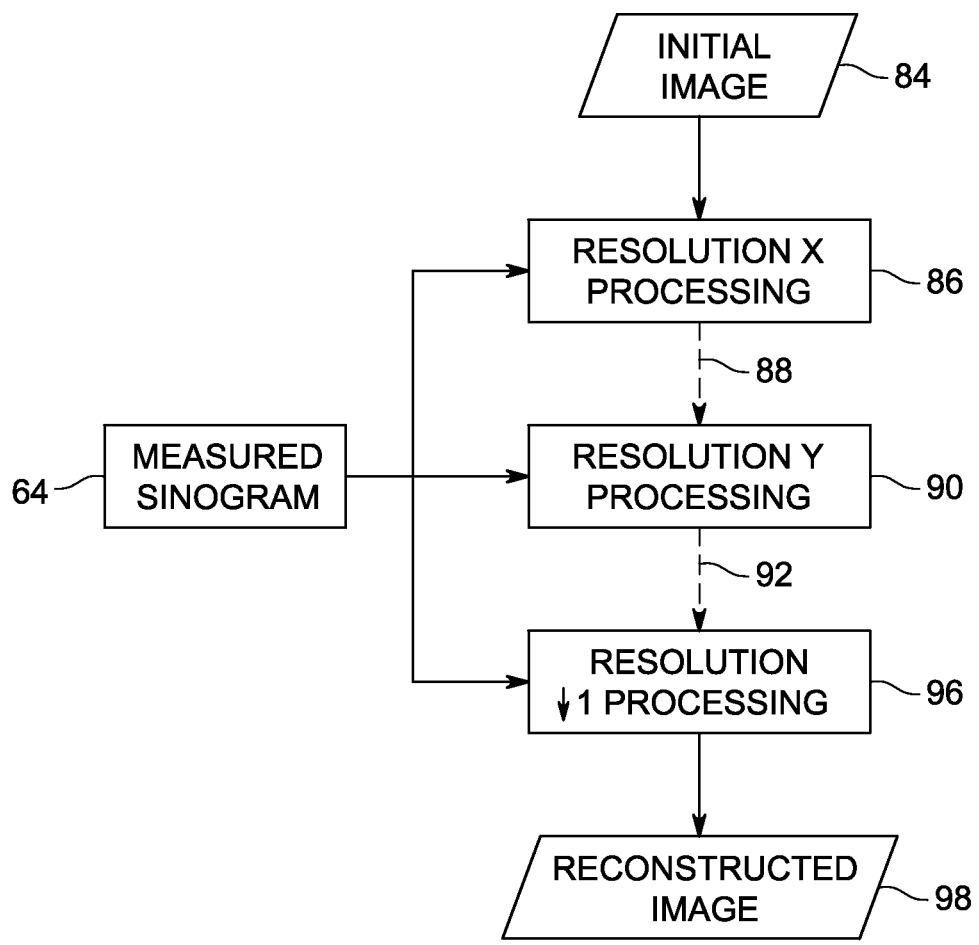
Figure 11:
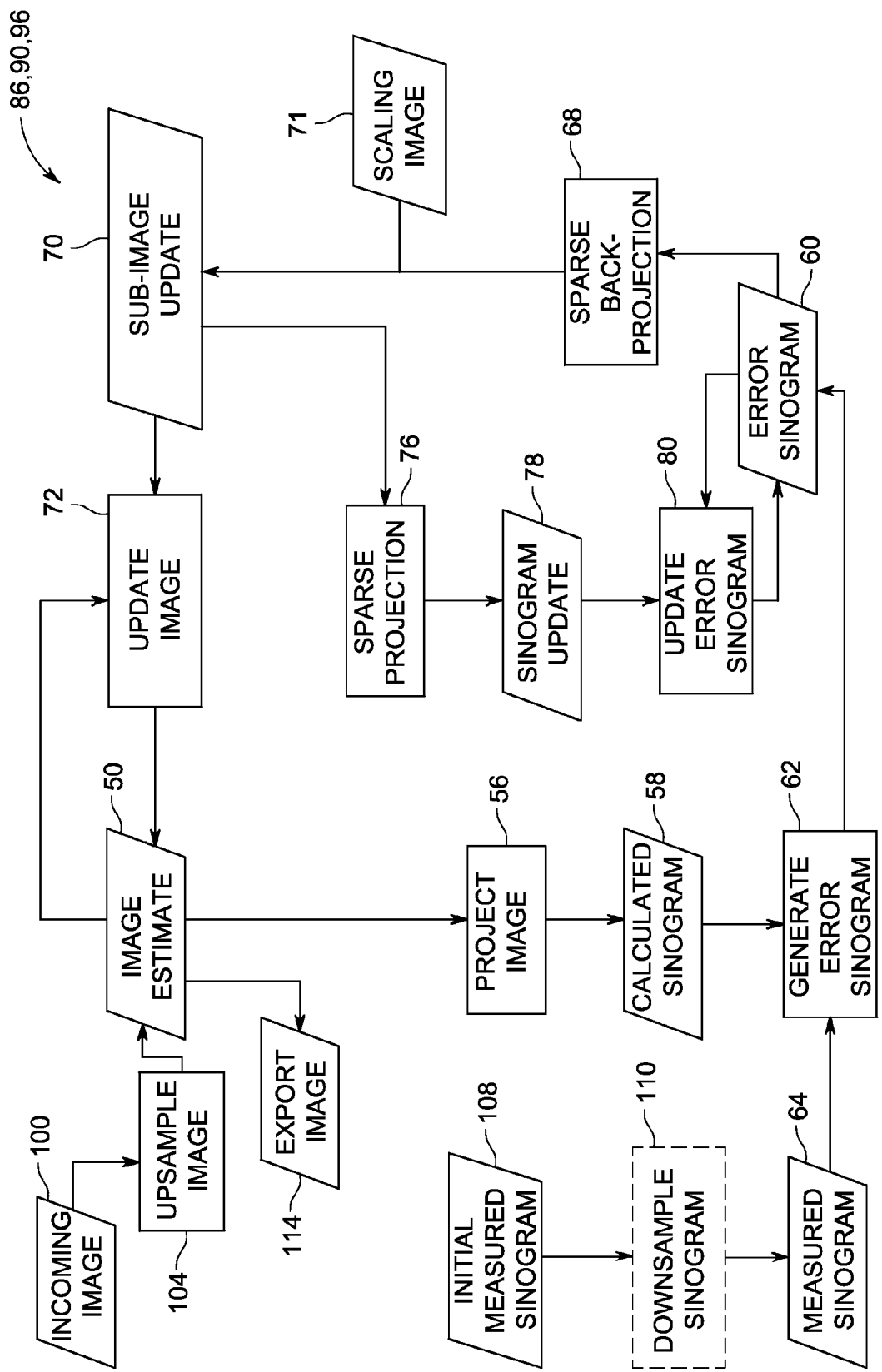

FIG. 8 is a graph comparing convergence rates of ICD reconstructions employing approximations of the Hessian matrices and reconstructions employing the complete Hessian matrices in the update step, in accordance with aspects of the present disclosure; and FIG. 9 is a graph comparing convergence rates of ICD reconstructions employing approximations of the Hessian matrices and reconstructions employing the complete Hessian matrices in the update step where the blocks of voxels being updated extend in the z-direction, in accordance with aspects of the present disclosure;

FIG. 10 is a flowchart depicting exemplary logic for implementing a portion of another iterative coordinate descent reconstruction algorithm, in accordance with aspects of the present disclosure; and FIG. 11 is a flowchart depicting exemplary logic for implementing another portion of the iterative coordinate descent reconstruction algorithm of FIG. 10.

DETAILED DESCRIPTION

The present disclosure relates to image reconstruction employing iterative reconstruction approaches in which blocks or subsets of pixels or voxels are simultaneously updated via direct inversion of a matrix (e.g., a Hessian matrix), corresponding to the respective subset of pixels or voxels. In certain implementations an approximation of the Hessian matrix may be employed, as opposed to the true Hessian matrix. Further, in certain embodiments enforcement of minimum values may be employed, such as to enforce non-negativity of the values being processed. In addition, in certain embodiments the subset of voxels may include voxels at different slice locations within the three-dimensional volume being imaged.

Figure 1:
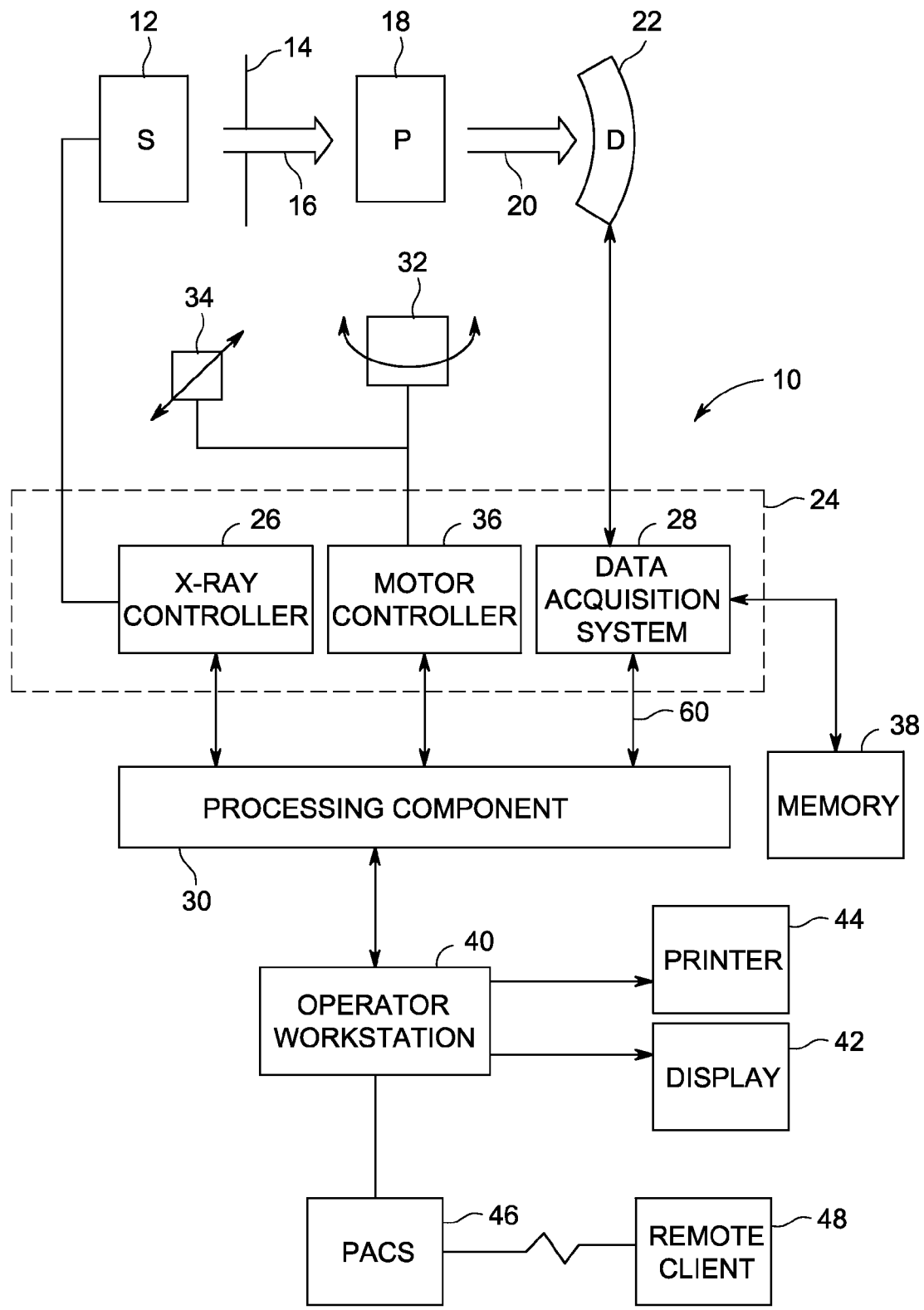
FIG. 1 is a diagrammatical view of an exemplary imaging system in the form of a CT imaging system for use in producing images in accordance with aspects of the present disclosure.

With the foregoing in mind, FIG. 1 illustrates diagrammatically an imaging system 10 for acquiring and processing projection data to produce reconstructed images. In the illustrated embodiment, system 10 is a computed tomography (CT) system designed both to acquire original image data, and to process the image data for display and analysis in accordance with the present technique. In other embodiments, the imaging system may be a positron emission tomography (PET) system, a single photon emission computed tomography (SPECT) system, or any other imaging system suitable for generating tomographic images. The depicted system 10 is configured to employ iterative reconstruction techniques in the processing of acquired or saved projection data to reconstruct medically useful images in accordance with the present disclosure. In the embodiment illustrated in FIG. 1, imaging system 10 includes a source of X-ray radiation 12 positioned adjacent to a collimator 14. In one exemplary embodiment the X-ray source 12 is an X-ray tube. In other embodiments the X-ray source 12 may be a solid-state or thermionic X-ray source, or may be other sources of X-ray radiation suitable for the acquisition of medical images.

The collimator 14 shapes and/or limits the beam of X-rays 16 that passes into a region in which an object, such as a subject of interest 18, is positioned. A portion of the X-ray radiation 20 passes through or around the subject and impacts a detector array, represented generally at reference numeral 22. Detector elements of the array produce electrical signals that represent the intensity of the incident X-rays 20. These signals are acquired and processed to reconstruct images of the features within the subject 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which commands acquisition of the signals generated in the detector 22. In the depicted embodiment, the system controller 24 acquires the signals generated by the detector using a data acquisition system 28. In this exemplary embodiment, the detector 22 is coupled to the system controller 24, and more particularly to the data acquisition system 28. The data acquisition system 28 receives data collected by readout electronics of the detector 22. The data acquisition system 28 typically receives sampled analog signals from the detector 22 and converts the data to digital signals for subsequent processing by a processor 30 discussed below. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the subject 18. It should be noted that the rotational subsystem 32 might include a gantry upon which the rotating components move. The linear positioning subsystem 34 enables the subject 18, or more specifically a patient support or table, to be displaced within an opening in the CT system 10. Thus, the table may be linearly moved within the gantry to generate images of particular areas of the subject 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that a plurality of radiographic views may be collected for processing. In the present context, system controller 24 also includes signal processing circuitry, typically based upon a general purpose or application-specific digital computer, associated memory circuitry for storing programs and routines executed by the computer (such as routines for executing image processing and reconstruction techniques described herein), as well as configuration parameters and image data, interface circuits, and so forth.

In the depicted embodiment, the image signals acquired and processed by the system controller 24 are provided to a processing component 30 for reconstruction of images. The processing component 30 may be one or more microprocessors and/or co-processors suitable for implementing projection, back-projection, and/or iterative reconstruction algorithms as discussed herein. The one or more processors and/or co-processors may execute such algorithms in a parallel or non-parallel implementation. The data collected by the data acquisition system 28 may be transmitted to the processing component 30 directly or after storage in a memory 38. It should be understood that any type of memory capable of storing a large amount of data might be utilized by such an exemplary system 10. Moreover, the memory 38 may be located at the acquisition system site or may include remote components for storing data, processing parameters, and routines for iterative image reconstruction described below.

The processing component 30 is configured to receive commands and scanning parameters from an operator via an operator workstation 40 typically equipped with a keyboard and other input devices. An operator may control the system 10 via the input devices. Thus, the operator may observe the reconstructed images and/or otherwise operate the system 10 via the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image, the image data, and optionally the variance data.

While the preceding discussion has treated the various exemplary components of the imaging system 10 separately, one of ordinary skill in the art will appreciate that these various components may be provided within a common platform or in interconnected platforms. For example, the processing component 30, memory 38, and operator workstation 40 may be provided collectively as a general or special purpose computer or workstation configured to operate in accordance with the present technique. Likewise, the system controller 24 may be provided as part of such a computer or workstation.

The projection algorithm implemented by the processing component 30 may be used for both forward projection (generating a sinogram from an image) and backward projection (generating an image from a sinogram), both of which are operations that are typically employed as part of an iterative reconstruction algorithm.

Examples of projection approaches include implementations that are pixel-driven or ray-driven. Fundamentally both the pixel-driven and ray-driven algorithms re-sample the sinogram or image values as a function of detector elements or pixels (respectively). For example, pixel-driven back-projection projects a line through the center of the image pixel of interest onto the detector array using the imaging geometry. Once a location of intersection on the detector is determined, a value is obtained from the detector (such as by linear interpolation) and the result is accumulated in the image pixel. In such a back-projection approach, a sinogram row is the source signal and an image row is the destination signal. For each image row, the pixel centers are mapped on to the detector. Pixel-driven projection is the transpose operation of the back-projection operation described above. Pixel-driven techniques are so named because the index of the main processing loop is the image pixel index.

Conversely, ray-driven projection generally consists of approximating each ray-integral by weighting and summing all image pixels that lie close to the ideal projection line. The ideal projection line may be approximated by projecting a line through the image to the center of the detector element of interest using the imaging geometry. A location of intersection is calculated for each image row (or column), a value is obtained from the image row, such as by linear interpolation, and the result is accumulated in the detector element. In such a projection approach, an image row is the source signal and a sinogram row is the destination signal. For each image row, the detector element centers are mapped on to the image row. Ray-driven back-projection is the transpose operation of the projection operation described above. In ray-driven techniques the index of the main processing loop is the projection line index. While ray-driven and projection-driven are suitable examples of projection implementations, other projection approaches may be used in conjunction with the present algorithms.

For example, an alternative projection algorithm is a distance-driven projection algorithm. The distance-driven projection approach can be summarized as the mapping of pixel and detector coordinates onto a common line or axis followed by a kernel operation. Distance-driven techniques are based upon the recognition that each view (i.e., source) position defines a bijection between the position on the detector and the position within an image row or column. Therefore, every point within an image row or column is mapped uniquely onto a point on the detector and vice versa. A length of overlap between each image pixel or voxel and detector element may, therefore, be defined. This overlap may be calculated by mapping all pixel or voxel boundaries in an image row or column of interest onto the detector or by mapping all detector element boundaries of interest onto the centerline of the image or column row of interest. In one embodiment, this is accomplished by mapping both image pixel and detector element boundaries onto a common line or axis by connecting all pixel boundaries and all detector element boundaries with the source and calculating the intercepts on the common axis. Based on these calculated intercepts, the length of overlap between each image pixel and each detector element can be calculated as seen on the common axis. A one-dimensional kernel operation may then be applied to map data from one set of boundaries to the other. The normalized length of overlap between each image pixel and detector cell may be used to define the weight used in projection and back-projection processes. The distance driven projection algorithm is well suited for iterative reconstruction and can be efficiently implemented in hardware. The distance-driven projection algorithm performs both forward-projection and back projection operations without artifacts, has low arithmetic complexity, and provides for sequential memory accesses. In addition, the distance-driven projection algorithm is symmetric with regard to the forward-projection and back-projection operations performed, allowing hardware resource sharing in a hardware implementation. As will be appreciated by those skilled in the art, this symmetry is useful in the context of some iterative reconstruction algorithms (such as conjugate gradients).

Selection of a suitable projection algorithm is only one aspect of implementing an iterative reconstruction algorithm in hardware. Another aspect of such an implementation is the selection of a completion criterion, such as a cost function that may be optimized or minimized to test for convergence or termination of the iterative process. Examples of cost functions include maximum-likelihood, maximum-a-posteriori, weighted least squares, and penalized weighted least squares. The latter is given by:

$$\sum_i w_i (p_i^k - p_i)^2 \quad (1)$$

where $w_i$ are the statistical weights for sinogram element i and p and $^P$ are the measured and calculated sinograms respectively. In one embodiment of the present technique, the quadratic term is replaced by a more general function, for example corresponding to a more heavily-tailed statistical distribution $\xi$. Correspondingly, the error sinogram in the first derivative of the cost function will undergo a non-linear transformation $\xi'$. For example, $\xi(p)$ can be a q-Generalized Gaussian function or a Generalized Geman function. In another example a double sigmoid function may be applied to the error sinogram $e(\Delta p)$:

$$e'(\Delta p) = e(\Delta p) \cdot s(\Delta p, \text{delta1}, \text{slope}) \cdot [1 - s(\Delta p, -\text{delta1}, \text{slope})] \quad (2)$$

where $$s(\Delta p, \text{delta}, \text{slope}) = 1/(1 + \exp(-\text{slope} \cdot (\Delta p - \text{delta}))) \quad (3)$$

As will be appreciated by those of ordinary skill in the art, similar transformations can be designed in order to maximize image quality, minimize image noise, maximize spatial resolution, and minimize image artifacts due to inconsistent data.

Yet another aspect of such an implementation is the selection of a suitable iterative reconstruction algorithm. One such iterative reconstruction algorithm is the iterative coordinate descent (ICD) algorithm. The baseline ICD technique operates by iterating over image pixels or voxels. Each pixel or voxel iterates in the inner loop over its corresponding sinogram data track. A typical ICD updated step is given by:

$$\mu_j^k = \begin{cases} \mu_j^{k-1} + \delta_j^k & j = \phi(k) \\ \mu_j^{k-1} & j \neq \phi(k) \end{cases} \quad (4)$$

$$\delta_\varphi^k = \frac{\sum w_i l_{i\varphi} (p_i - \hat{p}_i^{k-1})}{\sum w_i l_{i\varphi}^2} \quad (5)$$

where j is the pixel or voxel index, k is the sub-iteration number, and $\phi(k)$ specifies which pixel or voxel is updated in sub-iteration k, $\mu$ is the pixel or voxel value, p and $^P$ are the measured and calculated sinogram values, w are the weights from the weighted least squares cost criterion, and $l_{i\phi}$ is the contribution from pixel or voxel $\phi$ to sinogram element i.

In one embodiment, ICD is implemented using pixel or voxel subsets, which provide good parallelizability and computational performance. In particular, updating all pixels or voxels in a subset independently allows the update algorithm to be implemented in parallel. Furthermore, use of pixel or voxel subsets allows projection and back-projection steps (as discussed herein) to be implemented simultaneously and provides more uniform image convergence.

Figure 2:
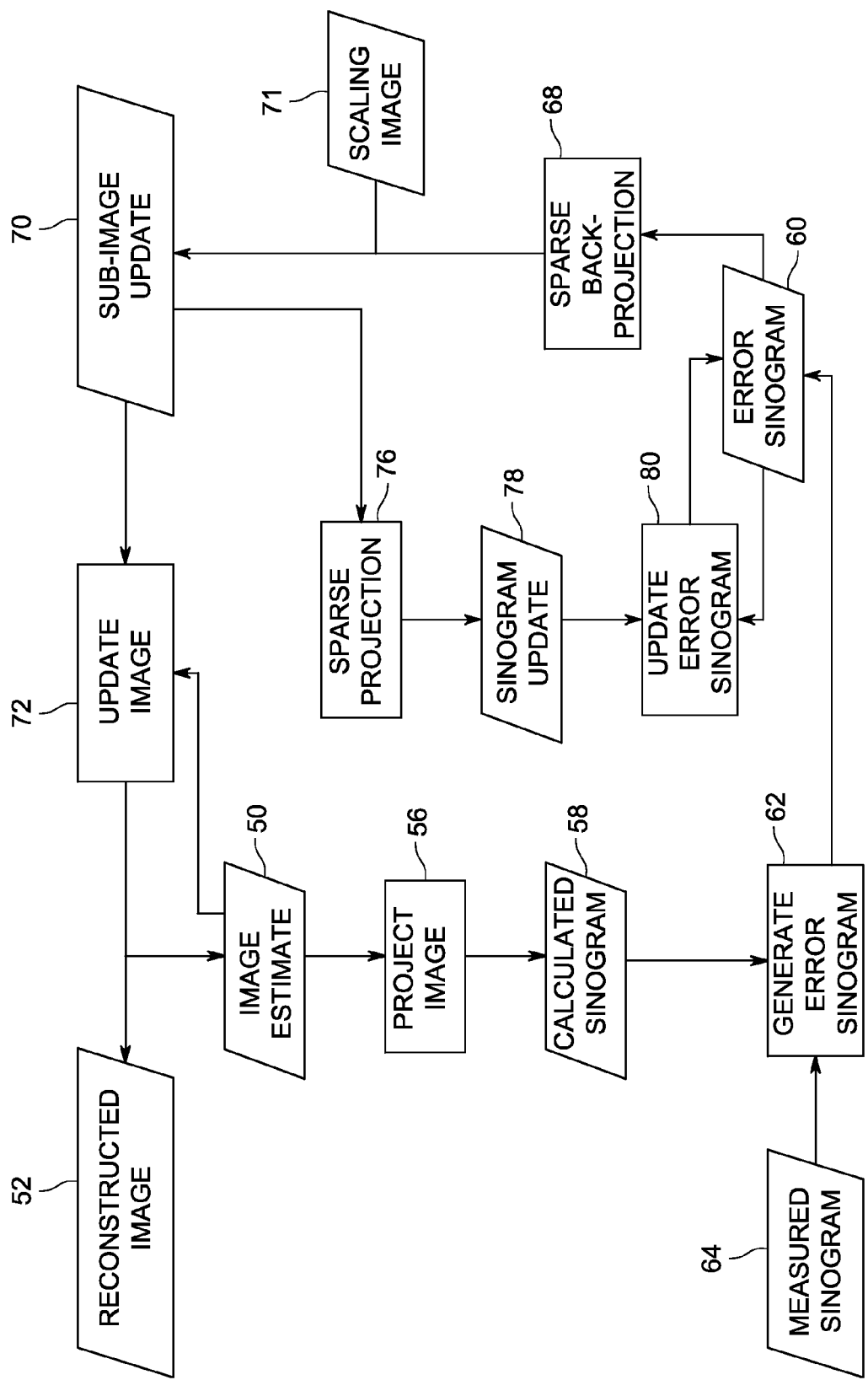
FIG. 2 is a flowchart depicting exemplary logic for implementing an iterative coordinate descent reconstruction algorithm, in accordance with aspects of the present disclosure.

An example of logic for iteratively implementing an ICD algorithm using pixel or voxel subsets is provided in FIG. 2. In the depicted example, an image estimate 50 (such as a direct reconstruction or filtered back projection of the raw image data) is provided. In instances where the image estimate 50 is converged, the converged estimate may be output as a reconstructed image 52. In one embodiment, the image estimate 50 is considered converged when the desired spatial resolution for the reconstructed image 52 is reached. In one embodiment, the update step is then given by:

$$\mu_j^k = \begin{cases} \mu_j^{k-1} + \delta_j^k & j \in \Phi \\ \mu_j^{k-1} & j \notin \Phi \end{cases} \quad (6)$$

where all the pixels or voxels belonging to subset $\Phi$ are updated simultaneously.

In one embodiment, pixel or voxel subsets are generated when the image estimate 50 is not converged and the ICD algorithm leverages the pixel or voxel subsets to accelerate image reconstruction. In one such embodiment, the image estimate 50 is divided into pixel or voxel subsets with each subset containing a number of pixels that are spatially separated, i.e., sparse or otherwise not neighboring. In other embodiments, however, the pixel or voxel subsets are selected such that each subset contains neighboring or proximate pixels or voxels, i.e., spatially localized "blocks" of pixels or voxels. The pixels or voxels in each subset can be processed concurrently, as described herein. In one embodiment, the pixel or voxel subsets are selected to minimize interactions of the respective sinogram tracks of the pixels or voxels within a subset. Every iteration of the exemplary technique consists of a number of sub-iterations. In each sub-iteration the pixels or voxels in one subset are simultaneously and independently updated (comparable to a number of Jacobi updates).

The image estimate 50 is projected (block 56) to generate a calculated sinogram 58. In one embodiment, the projection is done using a distance-driven algorithm or any other suitable forward projector. An error sinogram 60 is derived (block 62) from the calculated sinogram 58. The error sinogram 60 may be generated by various techniques. For example, in an exemplary implementation, a measured sinogram 64 derived from the projection data is subtracted from the calculated sinogram 58 to generate the error sinogram 60. In such an implementation, the projection data from which the measured sinogram 64 is derived is typically log corrected and in line-integral attenuation form. In other embodiments, the derivation of the error sinogram 60 may be based upon a suitable statistical model, such as a Poisson or least squares model.

In one embodiment, the error sinogram 60 is sparse back-projected (block 68), such as via distance-driven back-projection or any other suitable back-projector, based on a current pixel or voxel subset. The sparse back-projection step 68 generates a sub-iteration image update 70, corresponding to the current pixel or voxel subset, that may be used to update (block 72) the current image estimate. For example, in one embodiment, the image estimate 50 may be updated by subtracting the sub-iteration image update 70. In addition, the sub-iteration image update 70 may be sparse projected (block 76) based on the current pixel or voxel subset to generate a sinogram update 78. The sinogram update 78 and error sinogram 60 may then be used to update (block 80) the error sinogram for the next pixel or voxel subset sub-iteration. The process depicted by FIG. 2 may be repeated for different pixel or voxel subsets and image estimates 50 until convergence occurs and a reconstructed image is obtained. In one embodiment, the sparse distance-driven projection/backprojection is implemented similarly to the conventional distance-driven projection-backprojection, by modifying the loop over the pixel-/voxel-boundaries such that only the pixels or voxels belonging to the subset of interest are addressed, while all interleaving pixels, voxels, or image rows or columns that do not belong to the subset of interest are skipped.

In another embodiment, the image update 70 may be multiplied by a scaling image 71 prior to subtraction from the image estimate 50. This scaling image 71 may be chosen to improve the convergence properties of the iterative reconstruction algorithm. For example, the scaling image 71 may be obtained by taking an image of all ones, projecting this image using the current pixel or voxel subset, multiplying the resulting sinogram by a weight sinogram that measures the relative confidence in each sinogram pixel, and then backprojecting the weighted sinogram onto the current pixel or voxel subset. The reciprocal of the resulting image can then be used as a scaling image 71 to be multiplied by the image update 70 prior to subtracting it from image estimate 50.

While the above discussion relates to the processing of pixel or voxel subsets where the pixels or voxels in a subset are spatially separated, other types of pixel or voxel subsets may be employed in conjunction with ICD techniques. For example, as noted above, in one embodiment the pixel or voxel subsets that are simultaneously processed are block-based, i.e., neighboring or otherwise not spatially separated. The subsets of pixels or voxels can be selected in a variety of ways, some, but not all of which, are described herein. In general, each subset is a collection of one or more image pixels or voxels with no further restrictions.

For example in one three-dimensional implementation of a block-based update approach, a subset of voxels may be defined at various z positions and the same (x,y) positions. This approach may be suitable for use with the bandwidth-limited Hessian approximations discussed herein because the bandwidth can be chosen such that the majority of the correlation is considered or otherwise accounted for.

In another implementation, the subsets of voxels do not necessarily have to form a partition of the image volume. For example, a block with voxels A, B, C, and D may be initially considered or processed and, subsequently, a block with voxels C, D, E, and F may be considered or processed. That is, certain block constituents (e.g., voxels) may be shared between different blocks (i.e., overlapped). This may be particularly suitable for voxels near the edges or borders of the respective blocks and may help maintain smoothness or uniformity at the block edges or borders. This could be used, for example, to reduce or prevent visual artifacts that may otherwise be present if the blocks are not overlapped.

In addition, subsets or blocks may be chosen such that certain portions of the image are more frequently updated. For example, certain voxels along the edges of objects may be selected more frequently such that these voxels are more frequently updated. This could also be combined with the overlapping approach discussed above to overlap the selections along edges.

With respect to the actual update process, in one implementation, each iteration of the ICD algorithm includes multiple sub-iterations and each sub-iteration simultaneously updates a different subset or block of neighboring or proximate pixels or voxels via an n×n inversion. For example, in one embodiment, a block of adjacent pixels or voxels are updated by a direct inversion technique, such as by inverting the Hessian matrix associated with the respective subset of pixels or voxels:

$$x_j = A_{\varphi j}^{-1} y_\varphi \tag{7}$$

where $$y_\varphi = \left[\sum_i w_i l_{i\varphi}(p_i - p_i^{k-1})\right] \tag{8}$$

$$A_{\varphi j} = \left[\sum_i w_i l_{ij} l_{i\varphi}\right] \tag{9}$$

$$x_j = [\delta_j^k]. \tag{10}$$

In this embodiment, this process is repeated for all the blocks (or pixel or voxel subsets) and for all iterations.

While the preceding describes an image reconstruction in which the pixels or voxels within a subset are updated simultaneously by via direct inversion of a Hessian matrix corresponding to the subset, in other embodiments an approximation of the Hessian matrix may be employed instead of the true Hessian matrix.

One method of approximating the Hessian matrix involves limiting extent or regions of the Hessian matrix that are considered, such as to account for symmetry in the matrix or other data redundancies. For example, in one implementation, the maximum considered bandwidth of the Hessian matrix (e.g., a tridiagonal or pentadiagonal matrix) may be limited based on known or expected symmetries or redundancies. An additional case is a diagonal matrix, in which case a simultaneous update may be performed on a subset of voxels without considering the correlation between them. The limited bandwidth case may be effective when considering voxels aligned along the z direction at the same (x,y) location because the correlation is geometrically constrained to some z extent (e.g., to neighboring or proximate voxels), which translates to the limited bandwidth of the Hessian matrix. The bandwidth may be further limited so as to account for first-order correlation while ignoring lower-order correlation. The benefit of this approach is that limiting the bandwidth of the matrix eases the computational burden of computing the Hessian matrix (e.g., the cost scales quadratically with block size for the unlimited case and linearly with the block size for the tridiagonal case) as well as simplifying the matrix inversion.

In addition, in another implementation an approximation of the Hessian matrix may be based on the observation that the geometric correlation between two voxels is approximately space-invariant in certain portions of the object domain. Thus, the Hessian computation requirements can be reduced by exploiting this property to obtain an approximation for the correlation between the voxels of the considered subset. When also considering the projection domain statistical weighting, the spatially-invariant approximation may be less accurate. In that case, the weighting can be approximated in the image domain. The spatial-invariance could also be considered to hold within some region with the correlation varying from region to region.

In yet another embodiment, the approximation of the Hessian matrix may be analytically computed. For example, a parameterized analytic function may be employed that produces an approximation of the correlation between two voxels given their locations. This approach could also employ an image-based approximation to the projection-space statistical weighting data and include those weighting approximations in the analytic model.

Further, as will be appreciated, one or more of the above approaches for approximating the Hessian matrix may be employed or a particular approach may be differentially applied based on voxel or subset specific considerations. That is, the various Hessian approximation models may be mixed or differentially applied during the same reconstruction to derive the approximated Hessian matrix for each subset of voxels undergoing reconstruction. For example, different bandwidth limiting approximations may be employed depending on the voxels being updated. If a subset of voxels appears to be outside of the object, a diagonally approximated Hessian (bandwidth=1) may be applied whereas, if the subset appears to be inside of the object, a tridiagonally (bandwidth=3) Hessian approximation may be applied. Furthermore, in one hybrid approach, complete (i.e., not approximated) Hessian matrices may be employed for certain subsets of pixels or voxels and approximated Hessian matrices employed for others. That is, in one hybrid approach the approximated Hessian matrices may only be employed for certain of the subsets (such as where the approximation is estimated to provide to substantially replicate the use of the true or full Hessian matrix) while the remainder of the subsets may be processed using an approximation of the Hessian matrix.

With the foregoing discussion of approaches for selecting blocks of pixels or voxels and approaches for approximating the Hessian matrix in mind, in one implementation a group update calculates the updates for a subset without considering the correlation among voxels. In such an implementation, this is equivalent to using a limited bandwidth Hessian with bandwidth equal to 1. The block and group methods can be combined so that updates for multiple subsets are computed using one of the approaches above, but without considering correlations between any two voxels from different subsets. This approach provides further parallelization opportunity. It can also be considered a special-case of the Hessian approximation where we are applying different approximations to different subsets.

While using an approximation of the Hessian matrix in place of the complete or true Hessian matrix for subset-based iterative reconstruction is one approach that may be employed to improve computational performance, other approaches may also be employed to improve performance. For example, in certain implementations, limitations (i.e., minimum and/or maximum values) may be enforced with respect to the values produced during reconstruction. One example would be restrict or limit reconstructed values to greater than or equal to zero when the physical quantity being reconstructed cannot have a negative value, which is the case for X-ray computed tomography. Likewise, positive values may be limited (i.e., have a maximum) based on X-ray source characteristics, system or scan geometry, assumed scanned object attenuation characteristics, and/or scan protocol (i.e., based on what range of X-ray incidence is physically possible or likely). With the foregoing in mind, the following implementation examples describe approaches that may be employed to enforce minimum or maximum reconstructed values, such as by enforcing non-negativity.

One approach for handling non-negativity is to clamp (i.e., restrict) any voxel that would otherwise be updated to a negative value to zero. That is, instead of updating a voxel to a negative number, the voxel value is instead set to zero. This is a straightforward approach when the subsets only contain a single voxel. However, when subsets contain multiple voxels, the inversion of the Hessian matrix produces an update that is only optimal in a joint sense. That is, if some voxels in the subset are set to zero to avoid a negative result, the overall update may be sub-optimal due to the change in direction of the resulting voxel subset update caused by setting some of the voxel values to zero. In addition, the minimum can be specified as a value less than or greater than zero. For example, enforcing a minimum of less than zero may be meaningful in cases involving noisy data where strict non-negativity yields undesirable image characteristics.

In one embodiment, relaxed solves may be employed to compute a relaxation factor for the update, such that applying the update will not generate any negative values. For example, if one voxel will be updated from +1 to −1 and all other voxels in the subset will remain non-negative, the update may be applied to the entire subset with a relaxation factor of 0.5. This approach maintains the intended direction of the update calculated by the inversion of the Hessian matrix. However, it could also produce updates with step-sizes of 0 when a voxel with a value of 0 would be updated to be negative, i.e., updates for a voxel or subset of voxels are effectively stopped before a voxel value within the subset goes below zero.

In another embodiment, a recursive solve approach may be employed which first applies clamped updates to any voxel in the subset that would be updated to be negative, but does not initially update the remaining voxels in the subset. The clamped voxels are then removed from the subset and the now-smaller subset is solved separately. In such an implementation, the subset shrinks at every step, so this approach will terminate in a finite number of steps, i.e., when the number of voxels in a subset goes to zero.

A further approach is to hybridize the above-described methods. In addition, these approaches for enforcing minimum and/or maximum values can be combined with the Hessian approximation hybrids discussed herein as well. As mentioned with respect to relaxed solves above, the inclusion of a voxel with value of zero introduces the possibility of not updating the entire subset. Similarly, voxels with values close to zero can restrain the step-size to be very small. Thus, separate approaches can be applied to subsets depending on the values of the voxels within the subset. If there are many small values, then a clamped update can be applied, potentially with a lower bandwidth Hessian approximation. Subsets with no small values are less likely to produce negative values and thus could be updated with a suitable approach as discussed above. Furthermore, other hybrid approaches can be produced by switching from one method to another based on the circumstances. For example, a relaxed solve may be employed until such time as the relaxation factor is determined to be too small (i.e., below a specified threshold), at which time a clamping approach may instead be employed.

Figure 3:
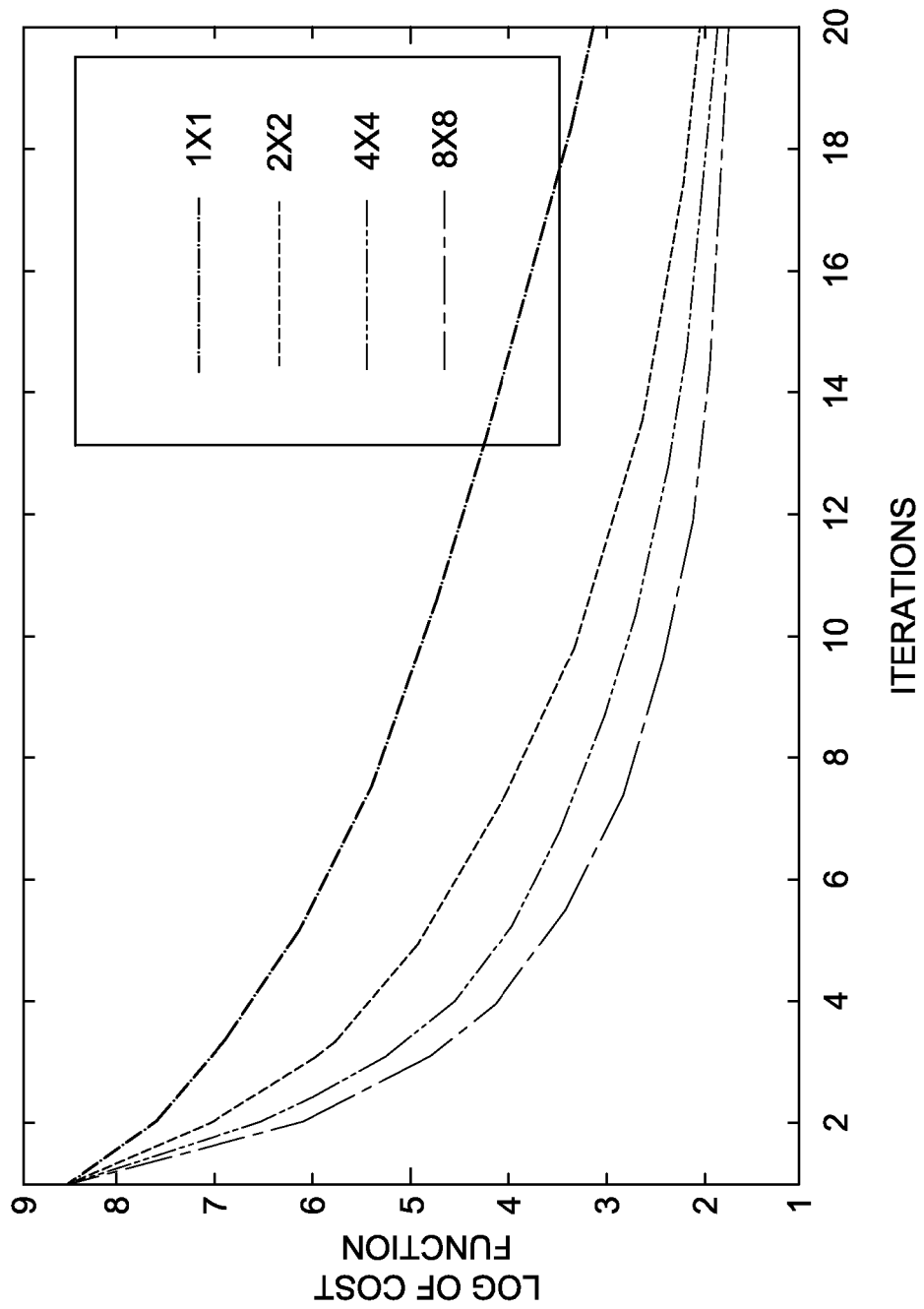
FIG. 3 is a graph depicting convergence rates of a block-based ICD reconstruction with negativity allowed and raster ordered processing, in accordance with aspects of the present disclosure.
Figure 4:
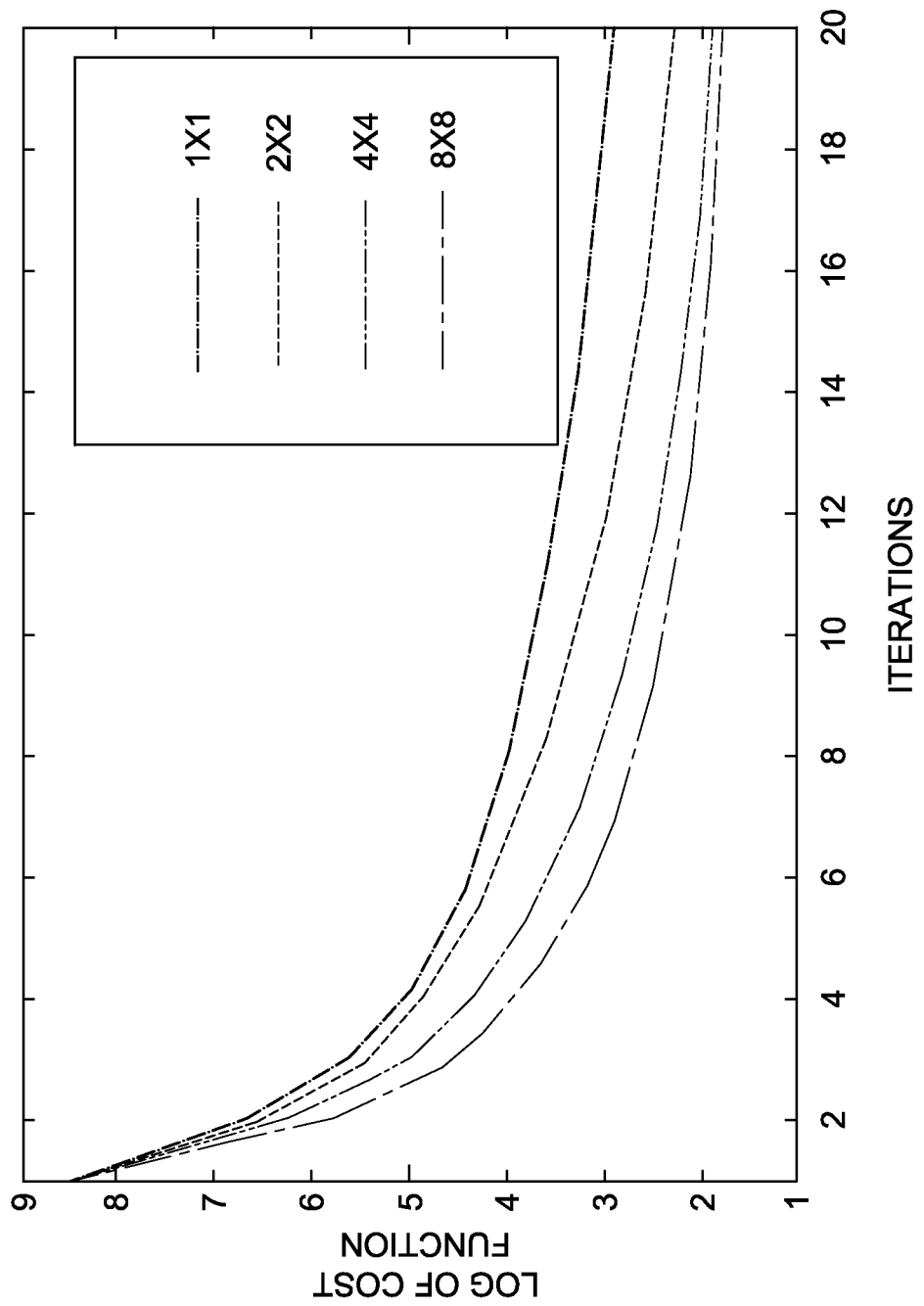
FIG. 4 is a graph depicting convergence rates of a block-based ICD reconstruction with negativity allowed and random ordered processing, in accordance with aspects of the present disclosure.

With the foregoing discussion in mind, various examples of convergence rates are provided to demonstrate the differences observed using one or more of the approaches discussed herein. For example, turning to FIGS. 3 and 4 these figures depict examples of block-based ICD reconstructions using different block sizes (i.e., 1×1, 2×2, 4×4, 8×8) and a quadratic regularization where non-negativity is not enforced and where processing is initialized with a noisy solution. In the examples of both FIGS. 3 and 4, the complete Hessian matrix is employed for the update steps. FIG. 3 depicts an example where processing proceeds in a raster ordered fashion while FIG. 4 depicts an example where processing proceeds in a random order. As evidenced in these examples, increasing block size improves convergence rates though, with negative values allowed (i.e., non-negativity not enforced), convergence may take more than 10 iterations to achieve.

Figure 5:
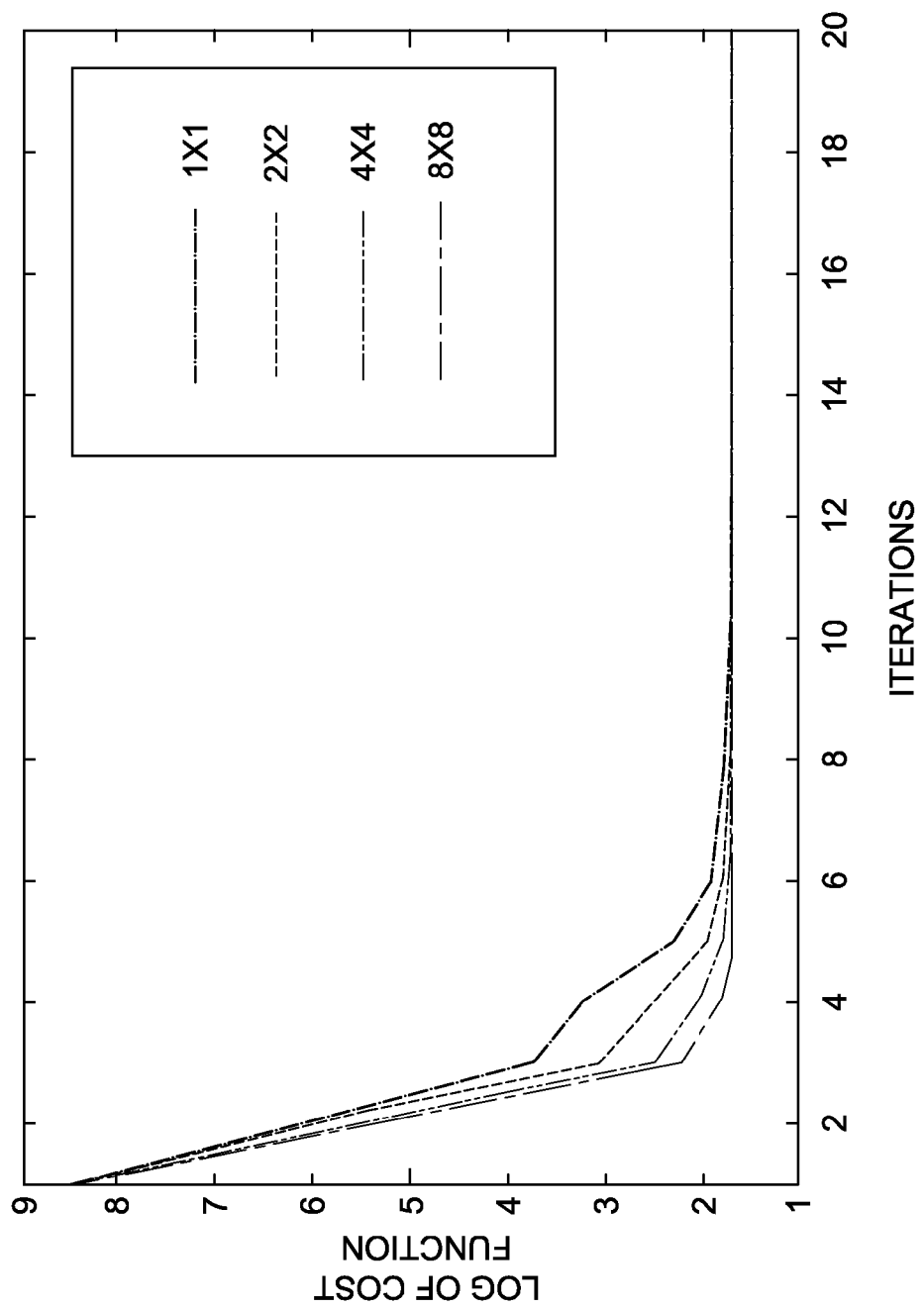
FIG. 5 is a graph depicting convergence rates of a block-based ICD reconstruction with non-negativity enforced and raster ordered processing, in accordance with aspects of the present disclosure.
Figure 6:
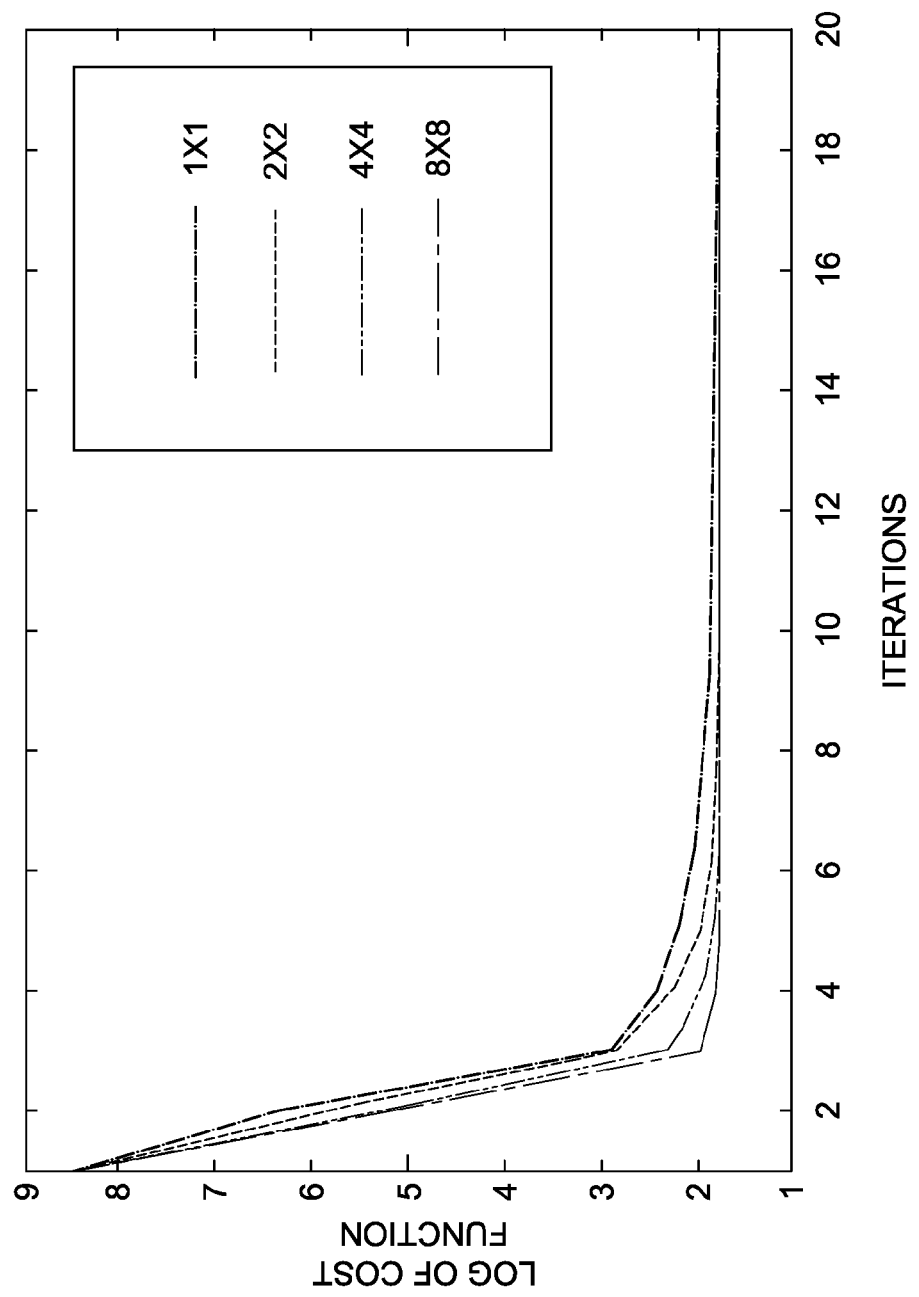
FIG. 6 is a graph depicting convergence rates of a block-based ICD reconstruction with non-negativity enforced and random ordered processing, in accordance with aspects of the present disclosure.

Turning to FIGS. 5 and 6, examples are depicted that correspond respectively to FIGS. 3 and 4 but in which non-negativity is enforced during the update process to prevent updates to negative values. In these examples, the convergence rates for block-based ICD reconstructions using different block sizes and a quadratic regularization are depicted where processing is initialized with a noisy solution. In the examples of both FIGS. 5 and 6, the complete Hessian matrix is employed for the update steps. FIG. 5 depicts an example where processing proceeds in a raster ordered fashion while FIG. 6 depicts an example where processing proceeds in a random order. As seen in the previous examples, increasing block size improves convergence rates. However, with non-negativity enforced, convergence may effectively occur in less than eight iterations.

Figure 7:
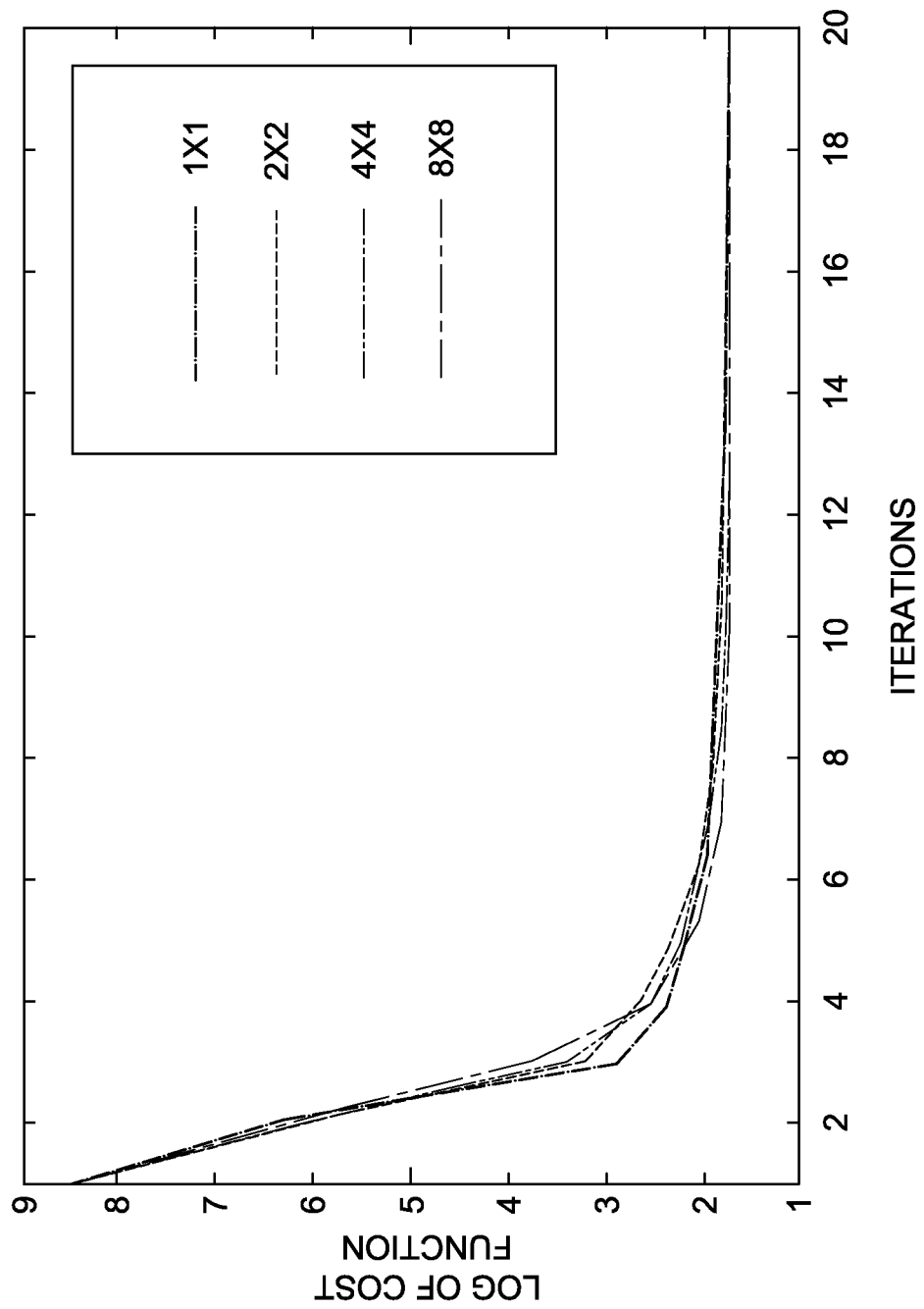
FIG. 7 is a graph depicting convergence rates of an ICD reconstruction in which an approximation of the Hessian matrix is employed in the update step, in accordance with aspects of the present disclosure.

In FIG. 7, an example of block-group based ICD reconstruction is depicted where an approximation of the Hessian matrix is employed in the update step. In this example, the block group employed has a bandwidth approximation of 1. The convergence rates for the respective reconstructions using different block sizes, quadratic regularization, and enforcement of non-negativity are depicted where processing is initialized with a noisy solution. In addition, FIG. 7 depicts an example where processing proceeds in a random ordered fashion. By using an approximation of the Hessian matrix and enforcement of non-negativity, convergence may effectively occur in less than eight iterations.

In FIG. 8 an example is depicted comparing a block based ICD reconstruction and block-group based ICD reconstruction, both employing random ordering and quadratic regularization with non-negativity enforced. The block-group based ICD reconstruction employs an approximation of the Hessian matrix during the update step while the block-based approach employs the complete Hessian matrix. While similar performance is depicted in terms of iterations until convergence, the block-group based approach may use less computational power to reach convergence and/or may do so more quickly.

Lastly, FIG. 9 depicts an example of convergence rates in which the blocks of voxels extend in the z-direction. In this example, a complete (i.e., full) Hessian matrix is compared to a tridiagonal block matrix approximation of the full Hessian matrix. Performance is nearly identical for the two reconstructions, though the reconstruction employing the approximation of the Hessian matrix may use less computational power and/or may be performed more quickly. In both cases, the blocks employed are 1×4 blocks in z.

While the proceeding describes certain embodiments of block-based reconstruction approaches, further modifications are also possible. For instance, in an example of a least squares implementation, the use of pixel subsets may be combined with multi-resolution processing, as depicted in FIGS. 10 and 11, to improve convergence properties. In such an embodiment, an iteration performed at a lower resolution may generate an image which is then processed at a higher resolution, and so forth, until an image of the desired resolution is generated. For example, referring now to FIG. 10, an initial image estimate 84 may be processed at a first resolution (block 86) using pixel subsets and ICD techniques and based upon a measured sinogram 64. The output 88 of the processing may be the input for a subsequent processing step at a higher resolution and so forth. Intermediate resolution processing steps (block 90) likewise employ pixel subsets and ICD processing techniques along with measured sinogram data 64 to generate additional outputs 92 for subsequent processing. At the highest resolution processing step (block 96) the output of the preceding iteration is the input for the ICD iteration, along with the measured sinogram data 64. The output of the highest resolution processing step (block 96) is the reconstructed image 98, which may be displayed or otherwise provided to a clinician for review or analysis.

Referring now to FIG. 11, the iterated processing steps 86, 90, 96 are described in greater detail. In this depiction, an incoming image 100 is provided. The incoming image 100 may be the initial image, such as an image generated as a filtered backprojection of the original projection data, for the first iteration, or may be the output of a preceding iteration. Where the incoming image 100 is an output of a preceding processing iteration, the incoming image may be upsampled (block 104) to the next higher resolution of interest, thereby generating the image estimate 50. Upsampling may not occur however, where the incoming image 100 is not the output of a preceding iteration step, such as during the initial iteration. In an alternate embodiment, the incoming image 100 may be of a lower resolution (e.g., a low resolution filtered backprojection reconstruction), and may require upsampling prior to its use as the initial image in the iterative reconstruction. Generally, iterations can be performed at one or more different spatial resolutions, switching from lower to higher (or vice versa) spatial resolution by performing up-sampling (or down-sampling) as appropriate.

As discussed with regard to FIG. 2, the image estimate 50 is divided into pixel subsets and the image estimate 50 is projected (block 56) to generate a calculated sinogram 58. An error sinogram 60 is derived (block 62) from the calculated sinogram 58. The error sinogram 60 may be generated by various techniques. In implementations employing a measured sinogram 64 derived from the projection data, the measured sinogram 64 may be derived from an initial measured sinogram 108, which is downsampled (block 110), when appropriate, to correspond to the resolution of the current iteration. In such an embodiment, the measured sinogram 64 may be subtracted from the calculated sinogram 58 to generate the error sinogram 60. In such an implementation, the projection data from which the measured sinogram 64 is derived is typically log corrected and in line-integral attenuation form. In other embodiments, the derivation of the error sinogram 60 may be based upon a suitable statistical model, such as a Poisson or least squares model.

In the depicted embodiment, the error sinogram 60 is sparse back-projected (block 68) based on the current pixel subset, as discussed with regard to FIG. 2. The sparse back-projection step 68 generates a sub-iteration image update 70, corresponding to the current pixel subset, that may be used to update (block 72) the current image estimate. The updated image estimate may undergo further processing or, if all sub-iterations of the iteration are complete, may be exported as an export image 114. If additional iterations remain, the export image 114 may be the incoming image 100 for the next iteration. In no iterations remain, the export image 114 is the reconstructed image 98.

The sub-iteration image update 70 may also be sparse projected (block 76) based on the current pixel subset to generate a sinogram update 78. The sinogram update 78 and error sinogram 60 may then be used to update (block 80) the error sinogram for the next pixel subset sub-iteration, as described with regard to FIG. 2.

For example, in an exemplary embodiment, if the reconstructed image 98 is to be a 512×512 pixel image, a three iteration schedule may be employed. The first iteration may comprise a 128×128 pixel image which is processed using 4×4 pixel subsets, each subset consisting of 32×32 pixels, and $2^n$ (here $2^4$) iterations. The output of the processing at the first resolution may be upsampled to form a 256×256 pixel image which is processed using 8×8 pixel subsets, each subset consisting of 32×32 pixels, and $2^2$ iterations. The output of the processing at the second resolution may be upsampled to form a 512×512 pixel image which is processed using 16×16 pixel subsets, each subset consisting of 64×64 pixels, and $2^1$ iterations. As one of ordinary skill in the art will appreciate, resolutions, iterations for each resolution, number of pixels per subset, relaxation factor, and so forth are all factors that may be adjusted to achieve the desired computational and image quality properties.

In a further embodiment of the present approach, in order to improve convergence, at every sub-iteration corresponding to a certain pixel subset (whether neighboring or spatially separated), an update image is calculated and applied to the pixels in the subset, as described above. Likewise, as described above, the equivalent update to the error sinogram is calculated and applied to the sinogram. In addition, the equivalent update to the completion criterion, e.g., cost function, is calculated. After a desired number of sub-iterations (possibly every sub-iteration), an optimal linear combination of the last N updates is calculated that most nearly achieves the desired sinogram or cost function, i.e., the linear combination is calculated which minimizes the average error between the measured and calculated error sinograms.

For example, in one embodiment, in every sub-iteration, k, the pixel values, $\mu_j$, are incremented by $\delta_j^k$, which is zero for all the pixels j that do not belong to the subset $\Phi(k)$. After a user-defined number of iterations or sub-iterations, a number of previous updates $\delta_j^k$ are linearly combined in order to achieve faster convergence as given by the exemplary equation:

$$\mu_j^{new} = \mu_j + c_1 \cdot \delta_j^k + c_2 \cdot \delta_j^{k+1} + c_3 \cdot \delta_j^{k+2} + c_4 \cdot \delta_j^{k+3} + \ldots + c_N \cdot \delta_j^{k+N} \quad (11)$$

where $c_1, c_2, \ldots c_N$ are optimized by solving:

$$\mathrm{argmax}(\mu_j^{new}) \quad (12)$$

This optimization technique is known outside the area of image reconstruction as Krylov subspace optimization.

While in the present discussion reference is made to a CT scanning system in which a source and detector rotate on a gantry arrangement, it should be borne in mind that the present technique is not limited to data collected on any particular type of scanner. For example, the technique may be applied to data collected via a scanner in which an X-ray source and/or a detector are effectively stationary and an object is rotated, or in which the detector is stationary but an X-ray source rotates. Further, the data could originate in a scanner in which both the X-ray source and detector are stationary, as where the X-ray source is distributed and can generate X-rays at different locations. Further, the present technique could apply to three-dimensional or cone beam acquisitions as well as to two-dimensional acquisitions. Hence any reference to the word pixel should be understood as also encompassing a voxel in such three-dimensional contexts. In brief, it should be borne in mind that the system of FIG. 1 is described herein as only one example of a suitable system or type of system. Other system configurations and operational principles may, of course, be envisaged for acquiring and processing image data and variance data and for utilizing the data as discussed below. Furthermore, the approaches described herein may be applied to various other iterative tomographic reconstructions, such as those associated with positron emission tomography (PET) and single positron emission computed tomography (SPECT), in addition to CT. The approaches described herein may also be used in tomosynthesis reconstructions, where only a small number of view angles or a limited angular range of data are available. For example, the techniques discussed herein may be employed with penalized or unpenalized and/or weighted or unweighted least-squares iterative tomographic reconstruction techniques.

Technical effects of the invention include the iterative reconstruction of images in which blocks or subsets of pixels or voxels are simultaneously updated via direct inversion of a matrix corresponding to the block or subset of pixels or voxels. In one technical implementation, an approximation of the matrix (such as a Hessian matrix) may be employed. Other technical effects may include enforcement of minimum or maximum values during the update. Further technical effects may include updating voxels at different slice locations within the three-dimensional volume being imaged.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for iteratively reconstructing image data, comprising the steps of:
   accessing an initial image;
   defining a plurality of image element subsets of the initial image, wherein some or all of the plurality of image element subsets correspond to voxels aligned in z such that they share the same (x,y) location;
   iteratively generating updates to the initial image or a subsequent updated image based on the respective image element subsets, wherein at least one of the updates is generated by directly inverting a respective Hessian matrix or an approximation of a respective Hessian matrix associated with a corresponding image element subset; and
   terminating the iterative generation of updates upon satisfaction of a completion criterion.

2. The method of claim 1, wherein the image element subsets comprise one of pixel subsets or voxel subsets.

3. The method of claim 1, wherein the approximation of the respective Hessian matrix comprises a Hessian matrix in which only a limited bandwidth is considered.

4. The method of claim 1, wherein the approximation of the respective Hessian matrix accounts for spatial-invariance within the object domain.

5. The method of claim 1, comprising computing the approximation of the respective Hessian matrix using a parameterized analytic function that produces an approximation of the correlation between two voxels given their locations.

6. The method of claim 1, wherein the iteratively generated updates are limited such that the updates, when applied, do not result in updated values above a maximum or below a minimum.

7. The method of claim 1, wherein the iteratively generated updates are limited such that the updates, when applied, do not result in negative values.

8. The method of claim 1, comprising computing a relaxation factor for a respective iteratively generated update such that applying the update will not generate a negative value.

9. The method of claim 1, wherein two or more of the plurality of image element subsets have image elements in common.

10. The method of claim 1, wherein the iteratively generated updates are applied recursively such that image elements that would be updated to a negative value are set to zero and removed from the respective image element subset to generate a smaller image element subset that is updated separately.

11. One or more non-transitory machine readable media, encoding one or more routines which, when executed by a processor, perform acts comprising:
generating an initial image;
iteratively updating a plurality of image element subsets of the initial image or of a subsequent updated image, wherein one or more of the updates is generated by directly inverting an approximation of a respective Hessian matrix associated with a corresponding image element subset, and wherein some or all of the plurality of image element subsets correspond to voxels aligned in z such that they share the same (x,y) location; and
terminating the iterative generation of updates upon satisfaction of a completion criterion.

12. The one or more non-transitory machine readable media of claim 11, wherein the one or more non-transitory machine readable media encodes a routine which, when executed by a processor, generates the approximation of the respective Hessian matrix by considering only a limited bandwidth of a corresponding complete Hessian matrix.

13. The one or more non-transitory machine readable media of claim 11, wherein the one or more non-transitory machine readable media encodes a routine which, when executed by a processor, generates the approximation of the respective Hessian matrix by approximating a correlation between voxels of the corresponding image element subset due to space invariance between voxels within the object domain.

14. The one or more non-transitory machine readable media of claim 11, wherein the one or more non-transitory machine readable media encodes a routine which, when executed by a processor, computes the approximation of the respective Hessian matrix using a parameterized analytic function that produces an approximation of the correlation between two voxels given their locations.

15. The one or more non-transitory machine readable media of claim 11, wherein the iteratively generated updates are limited such that the updates, when applied, do not result in negative values.

16. The one or more non-transitory machine readable media of claim 11, wherein the iterative updates are applied recursively such that image elements that would be updated to a negative value are set to zero and removed from the respective image element subset to generate a smaller image element subset that is updated separately.

17. A method for iteratively reconstructing image data, comprising the steps of:
accessing an initial image;
iteratively updating a plurality of image element subsets of the initial image or a subsequent updated image, wherein the iteratively generated updates are limited such that the updates, when applied, do not result in negative values, and wherein the iterative updates are applied recursively such that image elements that would be updated to a negative value are set to zero and removed from the respective image element subset to generate a smaller image element subset that is updated separately; and
terminating the iterative generation of updates upon satisfaction of a completion criterion.

18. The method of claim 17, wherein one or more of the updates are generated by directly inverting a respective Hessian matrix associated with a corresponding image element subset or directly inverting an approximation of the respective Hessian matrix.

19. The method of claim 17, wherein the iteratively generated updates are applied with a relaxation factor that prevents an image element from being updated to a negative value.

20. The method of claim 17, wherein some or all of the plurality of image element subsets correspond to voxels aligned in z such that they share the same (x,y) location.

* * * * *